United States Patent [19]  [11] 4,083,978
Budai et al.  [45] Apr. 11, 1978

[54] OXIME ETHERS

[75] Inventors: Zoltán Budai; Aranka Lay nee Kónya; Tibor Mezei; Katalin Grasser; Enikö Szirt nee Kiszelly; Ibolya Kosóczky; Lujza E. Petöcz, all of Budapest, Hungary

[73] Assignee: Egyt Gyogyszervegyeszeti Gyar, Budapest, Hungary

[21] Appl. No.: 652,806

[22] Filed: Jan. 27, 1976

[51] Int. Cl.$^2$ .................. A61K 31/495; C07D 295/12
[52] U.S. Cl. ................................. 424/250; 260/268 R; 542/429
[58] Field of Search ........... 260/240 F, 240 A, 240 R, 260/268 R; 424/250; 524/429

[56] References Cited
U.S. PATENT DOCUMENTS 3,526,671  9/1970  Judd ..................................... 260/566

Primary Examiner—Donald G. Daus
Assistant Examiner—Jose Tovar
Attorney, Agent, or Firm—Young & Thompson

[57] ABSTRACT

Oxime ethers of the formula

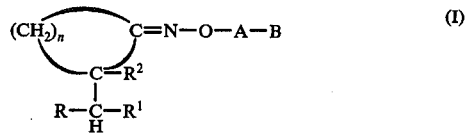

wherein
R stands for a phenyl group which may be substituted by a halogen chlorine atom or by one to three methoxy groups;
$R^1$ and $R^2$ denote each a hydrogen atom or together a valence bond;
A denotes a $C_2$-$C_4$ straight or branched-chain alkylene group;
B is piperazino having a benzyl or $C_{1-3}$ alkyl substituent on the nitrogen atom; and
n denotes an integer from 3 to 6, have nicotine-lethality inhibiting, tetrabenazine-antagonistic and antiepileptic effects.

2 Claims, No Drawings

OXIME ETHERS

This invention relates to novel oxime ethers possessing valuable therapeutic effects and their optical isomers and salts.

The noval compounds have the general formula I

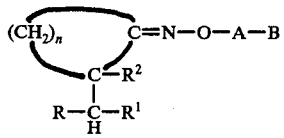

wherein
- R stands for a phenyl group which may be substituted by a chlorine atom or by one to three methoxy groups;
- $R^1$ and $R^2$ denote each a hydrogen atom or together a valence bond;
- A denotes a $C_2$-$C_4$ straight or branched-chain alkylene group; is piperazino having a benzyl or $C_{1-3}$ alkyl substituent on the nitrogen atom;
- n denotes an integer from 3 to 6.

The scope of the novel oxime ethers of the general formula I comprises obviously also all their possible stereoisomers and the mixtures thereof.

The novel compounds of the general formula I can be produced according to the invention in the following ways:

a. A ketone of the general formula II

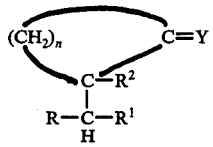

wherein R, $R^1$, $R^2$ and n have the same meaning as above, whereas Y denotes an oxygen or sulphur atom, is allowed to react with a hydroxylamine derivative of the general formula III $$H_2N - O - A - B \qquad (III)$$

wherein A and B have the above-specified meaning.

Ketones of the general formula II can be produced, e.g., in the way described in J. Am. Chem. Soc. 77, 624 /1955/ or in J. Chem. Soc. 1955, 1126, whereas hydroxylamine derivatives of the general formula III can be prepared, e.g., in the way described in J. Pharm. Sci. 58, 138 /1969/.

b. A chlorine compound of the general formula IV

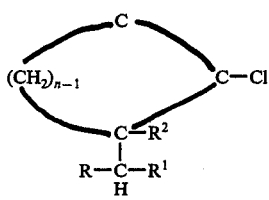

wherein R, $R^1$, $R^2$ and n have the same meaning as above, is allowed to react with a hydroxylamine derivative of the general formula III, wherein A and B have the above-specified meaning.

The compounds of general formula IV can be prepared by reacting 2-(p-chlorobenzal)-cyclohexanone with phosphorus oxychloride.

c. An oxime of the general formula V

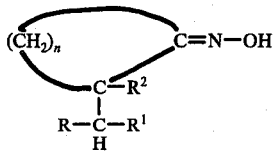

wherein R, $R^1$, $R^2$ and n have the same meaning as above, is reacted with a halogen alkylamine derivative of the general formula VI $$Hal - A - B \qquad (VI)$$

wherein Hal denotes a halogen atom, preferably a chlorine atom, whereas A and B have the above-specified meanings.

The oxime of the general formula V can be produced, e.g., in the way described in Org. Synth. Coll. Vol. II, p. 70.

d. A compound of the general formula V, wherein R, $R^1$, $R^2$ and n have the same meaning as above, is reacted with a dihaloalkane of the general formula VIII $$Hal - CH_2 - A' - Hal' \qquad (VIII)$$

wherein Hal and Hal' denote the same or different halogen atoms, whereas A' denotes a $C_1$-$C_3$ straight or branched-chain alkylene group, and the obtained halogen alkyl ether is aminated.

The reaction of the compounds of the general formula II and III (method a/) is carried out preferably in a solvent or a solvent mixture inert for the reaction. Solvents being inert for the reaction are, e.g., alcohols, preferably ethanol, or pyridine, triethyl amine etc. the temperature of the reaction can be varied within very wide limits. Though the reaction takes place according to our experience also at room temperature, the optimum reaction rate can be attained at the boiling point of the reaction mixture.

In the reaction of the compounds of the general formula IV and III (method b/) the components can be allowed to react in an inert solent, in the presence of a base. Suitable inert solvents are, e.g., diethyl ether, dibutyl ether, tetrahydrofurane, dioxane, etc., or aromatic or aliphatic hydrocarbons, such as benzene, toluene, xylene, hexane, cyclohexane, etc., whereas pyridine, triethyl amine, N-methyl morpholine, etc., can be applied as bases. The reaction can be carried out also without any inert solvent, using only the base as a solvent. The temperature of the reaction can be varied within wide limits. The upper limit is determined by the boiling point of the reaction mixture.

When the end products are to be produced by a reaction of the compounds specified by the general formulas V and VI (method c/), the reaction is to be carried out in an inert solvent, in the presence of a basic condensing agent. Benzene and its homologues, e.g., toluene, xylene, cumol, etc., can be mentioned as inert solvents. In this case preferably sodium amide or sodium hydride are applied as condensing agents. Obviously the same result can be atained also by other alkali metal amides or hydrides. In that case the use of alcohols, such as ethyl, propyl, butyl alcohols, proved to be the most suitable.

When an alkali hydroxide is applied as condensing agent, also water can be used as solvent.

When the compounds of the general formula I are produced by reacting compounds of the general formula V with those of the general formula VIII (method d/), the reaction can be carried out in a solvent or a solvent mixture inert for the reaction. Benzene and its homologues, such as toluene, xylene, cumol, etc., can be mentioned as inert solvents. In this case sodium amide or sodium hydride can be used as condensing agents. The same result can be attained on applying an alkali metal as condensing agent but in that case expediently ethanol is used as solvent. The amination of the obtained halogen alkyl ether is carried out under pressure in an autoclave, in the presence of the corresponding amine.

The compounds of the general formula I can be converted in a known way into acid addition or quaternary ammonium salts. For the preparation of the acid addition salts physiologically tolerable acids, such as hydrogen halides, sulphuric acid, phosphoric acid, citric acid, tartaric acid, fumaric acid, maleic acid, acetic acid, propionic acid, methane-sulphonic acid, succinic acid, etc., can be preferably applied. In order to prepare quaternary ammonium compounds the compounds of the general formula I are allowed to react with compounds suitable for quaternerization, e.g., with an alkyl halide or methanesulphonic acid ester.

The biological activity of the novel compounds according to the invention has been proved by a number of various tests. Of the observed effects the local analgesic, nicotine-lethanlity inhibiting, tetrabenazineantagonistic and antiepileptic effects were the most significant ones.

The inhibition of nicotine-lethality was determined on mice by the method of Stone (Stone, C.A. et al.: Arch. Intern. Pharmacodynamie 117, 419 /1958/) in groups of 10 mice each, at oral administration. The results are given in Table I.

Table I

| Compound (in Example) | LD$_{50}$ mg/kg | ED$_{50}$ mg/kg | Therapeutic index |
|---|---|---|---|
| 2 | 1450 | 43 | 33.7 |
| 10 | 600 | 56 | 10.7 |
| 6 | 650 | 43 | 15.1 |
| 7 | 400 | 11 | 36.4 |
| 15 | 1900 | 100 | 19.0 |
| 17 | 1200 | 40 | 30.0 |
| 18 | 1000 | 70 | 14.3 |
| Trihexyphenidyl (Artane) | 365 | 40 | 9.13 |

Therapeutic index = $\frac{LD_{50}}{ED_{50}}$

The antiepileptic effect was investigated on mice, at oral administration. Maximum electroshock (MES) was provoked by means of corneal electrodes, applying the known method of Swinyard (Swinyard et al.: J. Pharmacol. Exp. Ther. 106, 319–330 /1952/). The effect on tetracor-spasm was examined by the modified method of Banziger and Hane (Banziger, R. and Hane, L.D.: Arch. Int. Pharmacodyn. 167, 245–249 /1967/). The results are given in Table II.

Table II

| Compound (in Example) | LD$_{50}$ mg/kg | MES ED$_{50}$ mg/kg | Therapeutic index | Tetracor-spasm inhibition ED$_{50}$ mg/kg | Therapeutic index |
|---|---|---|---|---|---|
| 2 | 1450 | 150 | 9.7 | 50 | 29.0 |
| 1 | 620 | 105 | 5.9 | 74 | 8.4 |
| Trimethadion | | | | | |
| (Ptimal) | 2100 | 490 | 4.3 | 400 | 5.3 |

The tetrabenazine-reserpine antagonistic effect was investigated on mice in groups of 10 aminals each, at oral administration. The inhibition or suspension of the effect of the observed maximum dose was recorded, and the ED$_{50}$ values were calculated on the basis of the dose vs. effect curves. The results are shown in Table III.

Table III

| Compound (in Example) | LD$_{50}$ mg/kg | Tetrabenazine antagonism,ED$_{50}$ mg/kg | Therapeutic index | Reserpine antagonism ED$_{50}$, mg/kg | Therapeutic index |
|---|---|---|---|---|---|
| 1 | 620 | 7 | 88.6 | over 130 | 4.8 |
| 18 | 1000 | 28 | 36.0 | about 250 | 4 |
| Amitriptylin | 225 | 13 | 17.3 | 65 | 3.5 |

The new compounds of formula I and their methods of preparation are further illustrated by the aid of the following non-limiting Examples.

EXAMPLE 1

2-Benzal-1-(N-benzylpiperazinylpropoxyimino)-cyclohexane

A solution of 20.1 g (0.1 moles) of 2-benzalcyclohexanone-oxime in 200 ml anhydrous toluene is dropwise added at 85° C under stirring, to a suspension of 2.4 g (0.1 moles) of sodium hydride in 50 ml of anhydrous toluene. The mixture is kept for two hours at 130° C, then a solution of 27.8 g (0.11 moles) of N-benzylpiperazinylpropyl chloride in 50 ml of anhydrous toluene is added. The mixture is kept for 12 hours at 130° C, then cooled and shaken with a solution of 35 g of tartaric acid in 150 ml water. The aqueous phase is cooled to 0°–5° C and made alkaline to pH 10 with ammonium hydroxide. After extraction with dichloroethane, the solvent is distilled off and the residual crude phase processed to fumarate without any distillation.

Yield: 35 g (84.3%).
Difumarate: m.p. 196° C.
Citrate: m.p. 125°–126° C.
Maleinate: m.p. 190° C. (under decomposition).
Tartrate: m.p. 198°–200° C.
Iodomethylate: m.p. 134°–135° C. (under decomposition).
Hydrochloride: m.p. 211°–212° C.
Analysis: $C_{35}H_{43}N_3O_9$ Calculated: C, 64.70%; H, 6.67%; N, 6.46%. Found: C, 64.35%; H, 6.70%; N, 6.38%.

EXAMPLE 2

2-Benzal-1-(N-methylpiperazinylpropoxyimino)-cyclohexane

One proceeds in the way as specified in Example 1, with the difference that, instead of N-benzylpiperazinylpropyl chloride, 19.5 g (0.11 moles) of N-methylpiperazinylpropyl chloride are applied.

Yield: 27.4 g (80.5%).
Difumarate: m.p. 192° C.

Anaylsis: $C_{29}H_{39}N_3O_9$ Calculated: C, 60.71%; H, 6.85%; N, 7.32%. Found: C, 60.58%; H, 7.28%; N, 7.36%.

EXAMPLE 3

1-(N-Methylpiperazinylpropoxyimino)-2-(o-methoxybenzal)-cyclohexane

On starting from 2.4 g (0.1 moles) of sodium hydride, 23.1 g (0.1 moles) of 2-(o-methoxybenzal)-cyclohexanone oxime and 19.5 g (0.11 moles) of N-methylpiperazinylpropyl chloride, on proceeds in the way as specified in Example 1.

Yield: 35.2 g (95%).
Fumarate: m.p. 189°–191° C.
Analysis: $C_{30}H_{41}N_3O_{10}$. Calculated: C, 59.69%; H, 6.85%; N, 6.96%. Found: C, 59.43%; H, 7.00%; N, 6.92%.

EXAMPLE 4

1-(N-Methylpiperazinylpropoxyimino)-2-(m-methoxybenzal)-cyclohexane

On starting from 2.4 g (0.1 moles) of sodium hydride, 23.1 g (0.1 moles) of 2-(m-methoxybenzal)-cyclohexanone oxime and 19.5 g (0.11 moles) of N-methylpiperazinylpropyl chloride, one proceeds in the way as specified in Example 1.

Yield: 31.2 g (84.2%).
Fumarate: m.p. 187°–189° C.
Analysis: $C_{30}H_{41}N_3O_{10}$. Calculated: C, 59.69%; H, 6.85%; N, 6.96%. Found: C, 59.45%; H, 7.00%; N, 6.81%.

EXAMPLE 5

1-(N-Methylpiperazinylpropoxyimino)-2-(p-methoxybenzal)-cyclohexane

On starting from 2.4 g (0.1 moles) of sodium hydride, 23.1 g (0.1 moles) of 2-(p-methoxybenzal)-cyclohexanone oxime and 19.5 g (0.11 moles) of N-methylpipeazinylpropyl chloride, one proceeds in the way as specified in Example 1.

Yield: 30.5 g (82.5%).
Fumarate: m.p. 190° C.
Analysis: $C_{30}H_{41}N_3O_{10}$. Calculated: C, 59.69%; H, 6.85%; N, 6.96%. Found: C, 59.54%; H, 6.65%; N, 6.92%.

EXAMPLE 6

1-(N-benzylpiperazinylpropoxyimino)-2-(m-methoxybenzal)-cyclohexane

On starting from 2.4 g (0.1 moles) of sodium hydride, 23.1 g (0.1 moles) of 2-(m-methoxybenzal)-cyclohexanone oxime and 27.8 g (0.11 moles) of N-benzylpiperazinylpropyl chloride, one proceeds in the way as specified in Example 1.

Yield: 21.3 g (95.5%).
Difumarate: m.p. 195°–197° C.
Analysis: $C_{36}H_{45}N_3O_{10}$ Calculated: C, 63.61%; H, 6.67%; N, 6.18%. Found: C, 63.90%; H, 6.78%; N, 6.12%.

EXAMPLE 7

1-[2'-Methyl-3'-(4"-methylpiperazinylpropoxyimino)]-2-(p-methoxybenzal)-cyclohexane On starting from 2.4 g (0.1 moles) of sodium hydride, 23.1 g (0.1 moles) of 2-(p-methoxybenzal)-cyclohexanone oxime and 21.0 g (0.11 moles) of N-methyl-piperazinylisobutyl chloride, one proceeds in the way as specified in Example 1.

Yield: 32.5 g (84.4%).
Difumarate: m.p. 186°–190° C.
Analysis: $C_{31}H_{43}N_3O_{10}$ Calculated: C, 60.28%; H, 7.01%; N, 6.81%. Found: C, 59.92%; H, 7.25%; N, 6.74%.

EXAMPLE 8

1-(N-Methyliperazinylpropoxyimino)-2-(3',4'-dimethoxybenzal)-cyclohexane

On starting from 2.4 g (0.1 moles) of sodium hydride, 26.1 g (0.1 moles) of 2-(3',4'-dimethoxybenzal)-cyclohexanone oxime and 19.5 g (0.11 moles) of N-methylpiperazinylpropyl chloride, one proceeds in the way as specified in Example 1.

Yield: 34.1 g (85%).
Difumarate: m.p. 186°–188° C.
Analysis: $C_{31}H_{43}N_3O_{11}$ Calculated: C, 58.76%; H, 6.84%; N, 6.63%. Found: C, 58.58%; H, 6.64%, N, 6.61%.

EXAMPLE 9

1-(N-Methylpiperazinylpropoxyimino)-2-(3',4',5'-trimethoxybenzal)-cyclohexane

On starting from 2.4 g (0.1 moles) of sodium hydride, 29.1 g (0.1 moles) of 2-(3',4',5'-trimethoxybenzal)-cyclohexanone oxime and 19.5 g (0.11 moles) of N-methylpiperazinylpropyl chloride, one proceeds in the way as specified in Example 1.

Yield: 39.0 g (90.5%).
Difumarate: m.p. 185°–186° C.
Cyclamate: m.p. 166°–167° C.
Analysis: $C_{32}H_{45}N_3O_{12}$ Calculated: C, 57.92%; H, 6.83%; N, 6.33%. Found: C, 58.24%; H, 7.00%; N, 6.30%.

EXAMPLE 10

1-N-Benzylpiperazinylpropoxyimino)-2-(3',4',5'-trimethoxybenzal)-cyclohexane

On starting from 2.4 g (0.1 moles) of sodium hydride, 29.1 g (0.1 moles) of 2-(3',4',5'-trimethoxybenzal)-cyclohexanone oxime and 27.8 g (0.11 moles) of N-benzylpiperazinylpropyl chloride, one proceeds in the way as specified in Example 1.

Yield: 46.5 g (92%).
Difumarate: m.p. 188°–189° C.
Analysis: $C_{38}H_{49}N_3O_{12}$ Calculated: C, 61.6%; H, 6.7%; N, 5.7%. Found: C, 61.5%; H, 6.9%; N, 5.63%.

EXAMPLE 11

2-Benzal-1-[2'-methyl-3'-(4"-methylpiperazinyl)-propoxyimino]-cyclohexane

On starting from 2.4 g (0.1 moles) of sodium hydride, 20.1 g (0.1 moles) of 2-benzalcyclohexanone oxime and 20.76 g (0.11 moles) of 2-methyl-3-(4'-methylpiperazinyl)-propyl chloride, one proceeds in the way specified in Example 1.

Yield: 29.5 g (83%) of a pale yellow oil.
Difumarate: m.p. 190°–191° C.
Analysis: $C_{30}H_{41}N_3O_9$ Calculated: C, 61.31%; H, 7.03%; N, 7.15%. Found: C, 61.15%; H, 7.19%; N, 7.28%.

EXAMPLE 12

2-(m-Chlorobenzal)-1-[3'-(4''-methylpiperazinyl)-propoxyimino]-cyclohexane

On starting from 2.4 g (0.1 moles) of sodium hydride, 23.5 g (0.1 moles) of 2-(m-chlorobenzal)-cyclohexanone oxime and 19.5 g (0.11 moles) of N-methylpiperazinylpropyl chloride, one proceeds in the way as specified in Example 1.

Yield: 26.8 g (71.4%).

Difumarate: m.p. 194°–196° C.

Analysis: $C_{29}H_{38}ClN_3O_9$ Calculated: C, 57.25%; H, 6.3%; Cl, 5.84%; N, 6.4%. Found: C, 57.10%; H, 6.2%; Cl, 5.73%; N, 6.29%.

EXAMPLE 13

2-(p-Chlorobenzyl)-1-[3'-(4''-methylpiperazinyl)-propoxyimino]-cyclohexane

On starting from 2.4 g (0.1 moles) of sodium hydride, 23.74 g (0.1 moles) of 2-(p-chlorobenzyl)-cyclohexanone oxime and 19.5 g (0.11 moles) of N-methylpiperazinylpropyl chloride, one proceeds in the way as specified in Example 1.

Yield: 33.8 g (89.5%).

Difumarate: m.p. 194°–195° C.

Analysis: $C_{29}H_{40}ClN_3O_9$ Calculated: C, 57.09%; H, 6.60%; Cl, 5.31%; N, 6.89%. Found: C, 57.13%; H, 6.82%; Cl, 5.77%; N, 6.84%.

EXAMPLE 14

2-Benzal-1-[3'-(4''-methylpiperazinyl)-propoxyimino]-cycloheptane

On starting from 2.4 g (0.1 moles) of sodium hydride, 21.5 g (0.1 moles) of 2benzalcycloheptanone oxime and 19.5 g (0.11 moles) of N-methylpiperazinylpropyl chloride, one proceeds in the way as specified in Example 1.

Yield: 26.5 g (72.5%).

Difumarate: m.p. 196°–197° C (under decomposition).

Analysis: $C_{30}H_{41}N_3O_9$ Calculated: C, 61.31%; H, 7.03%; N, 7.15. Found: C, 61.20%; H, 6.94%; N, 7.10%.

EXAMPLE 15

2-Benzal-1-[3'-(4''-methylpiperazinyl)-propoxyimino]-cyclopentane

On starting from 2.4 g (0.1 moles) of sodium hydride, 18.7 g (0.1 moles) of 2-benzalcyclopentanone oxime and 19.5 g (0.11 moles) of N-methylpiperazinylpropyl chloride, one proceeds in the way as specified in Example 1.

Yield: 31.3 g (95.8%).

Difumarate: m.p. 205°–206° C (under decomposition).

Analysis: $C_{28}H_{37}N_3O_9$ Calculated: C, 60.09%; H, 5.66%; N, 7.51%. Found: C, 59.83%; H, 6.50%; N, 7.53%.

EXAMPLE 16

2-Benzal-1-[2'-methyl-3'-(4''-methylpiperazinyl)-propoxyimino]-cyclohexane

The solution of 20.1 g (0.1 moles) of 2-benzalcyclohexanone oxime in 200 ml of anhydrous toluene is dropwise added at 85° C, under continuous stirring, to the suspension of 2.4 g (0.1 moles) of sodium hydride in 10 ml of anhydrous toluene. After boiling the reaction mixture for 2 hours, 18.86 g (0.11 moles) of 1-bromo-3-chloro-2-methylpropane are added, and the reaction mixture is boiled for a few hours. After cooling the mixture to 80° C, a solution of 11 g (0.11 moles) of N-methylpiperazine in 20 ml of anhydrous toluene is dropwise added and the reaction mixture is kept for further 6 hours at this temperature. After cooling and washing with water, a solution of 22 g of fumaric acid in 220 ml of anhydrous ethanol is poured to the toluene solution, the mixture is cooled, and the precipitated crystals are filtered off. Yield in difumarate: 48 g (81.7%); m.p. 190°–191° C. The produce is identical with that described in Example 11.

EXAMPLE 17

1-(N-Methylpiperazinylpropoxyimino)-2-benzal-cyclooctane difumarate

On starting from 2.4 g (0.1 moles) of sodium hydride, 22.9 g (0.1 moles) of 2-benzalcyclooctanone oxime and 19.5 g (0.11 moles) of N-methylpiperazinylpropyl chloride, one proceeds in the way as specified in Example 1.

Yield: 33.8 g (95%).

Fumarate: m.p. 206°–207° C.

Analysis: $C_{31}H_{43}N_3O_9$ Calculated: C, 61.88%; H, 7.20%; N, 6.98%. Found: C, 61.38%; H, 7.05%; N, 6.92%.

EXAMPLE 18

2-Benzal-1-[3'-(4''-benzylpiperazinyl)propoxyimino]-cyclopentane difumarate

On starting from 2.4 g (0.1 moles) of sodium hydride, 18.7 g (0.1 moles) of 2-benzalcyclopentanone oxime and 27.8 g (0.11 moles) of N-benzylpiperazinylpropyl chloride, one proceeds in the way as specified in Example 1.

Yield: 37.4 g (94%).

Difumarate: m.p. 210°–211° C.

Analysis: $C_{34}H_{41}N_3O_9$ Calculated: C, 64.22%; H, 6.50%; N, 6.61%. Found: C, 64.12%, H, 6.61%, N, 6.60%.

What we claim is:

1. An oxime ether of the formula

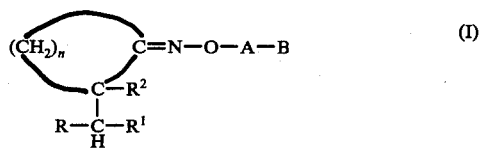

wherein
R denotes a phenyl radical which may be substituted by a chlorine atom or by one to three methoxy groups;
$R_1$ and $R_2$ denote a hydrogen atom each or together a valence bond;
A denotes a $C_2$–$C_4$ straight or branched-chain alkylene group;
B is piperazino having a benzyl or $C_1$–$C_3$ alkyl substituent on the nitrogen atom; and
n denotes an integer from 3 to 6,
and their pharmaceutically acceptable acid addition salts.

2. A pharmaceutical composition consisting essentially of a compound of claim 1, together with a pharmaceutically acceptable carrier.